(12) United States Patent
Chen et al.

(10) Patent No.: US 11,663,727 B2
(45) Date of Patent: May 30, 2023

(54) SYSTEMS AND METHODS FOR NON-INVASIVE CARDIAC ASSESSMENT

(71) Applicant: SHANGHAI UNITED IMAGING INTELLIGENCE CO., LTD., Shanghai (CN)

(72) Inventors: Xiao Chen, Lexington, MA (US); Shanhui Sun, Lexington, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 166 days.

(21) Appl. No.: 17/154,450

(22) Filed: Jan. 21, 2021

(65) Prior Publication Data

US 2021/0272297 A1 Sep. 2, 2021

Related U.S. Application Data

(60) Provisional application No. 62/983,017, filed on Feb. 28, 2020.

(51) Int. Cl.
 *G06T 7/00* (2017.01)
 *G06T 7/32* (2017.01)
 *A61B 5/318* (2021.01)
 *A61B 5/055* (2006.01)
 *A61B 5/00* (2006.01)

(52) U.S. Cl.
CPC .............. *G06T 7/32* (2017.01); *A61B 5/0035* (2013.01); *A61B 5/0044* (2013.01); *A61B 5/055* (2013.01); *A61B 5/318* (2021.01); *A61B 5/7267* (2013.01); *G06T 7/0012* (2013.01); *G06T 2207/10088* (2013.01); *G06T 2207/20081* (2013.01); *G06T 2207/20084* (2013.01); *G06T 2207/30048* (2013.01)

(58) Field of Classification Search
CPC ..................... G06T 7/32; G06T 7/0012; G06T 2207/10088; G06T 2207/20081; G06T 2207/20084; G06T 2207/30048; G06T 2207/20221; G06T 7/33; A61B 5/0035; A61B 5/0044; A61B 5/055; A61B 5/318; A61B 5/7267
USPC ......................................................... 382/131
See application file for complete search history.

(56) References Cited

U.S. PATENT DOCUMENTS

| | | | |
|---|---|---|---|
| 7,047,060 B1 * | 5/2006 | Wu ....................... | G01R 33/563 600/407 |
| 10,335,238 B2 * | 7/2019 | Kamen .................. | A61B 5/339 |
| 2011/0082359 A1 * | 4/2011 | Rey ........................ | A61B 5/327 600/411 |

(Continued)

*Primary Examiner* — Van D Huynh
(74) *Attorney, Agent, or Firm* — Zhong Law, LLC (57) ABSTRACT

Described herein are neural network-based systems, methods and instrumentalities associated with cardiac assessment. An apparatus as described herein may obtain electrocardiographic imaging (ECGI) information associated with a human heart and magnetic resonance imaging (MRI) information associated with the human heart, and integrate the ECGI and MRI information using a machine-learned model. Using the integrated ECGI and MRI information, the apparatus may predict target ablation sites, estimate electrophysiology (EP) measurements, and/or simulate the electrical system of the human heart.

20 Claims, 6 Drawing Sheets

(56) References Cited

U.S. PATENT DOCUMENTS

| | | | |
|---|---|---|---|
| 2016/0061920 A1* | 3/2016 | Mekkaoui | G06T 7/11 |
| | | | 382/131 |
| 2018/0253844 A1* | 9/2018 | Forman | G01R 33/5608 |
| 2021/0137384 A1* | 5/2021 | Robinson | A61B 5/0044 |
| 2021/0244340 A1* | 8/2021 | Yomtov | G16H 50/50 |

* cited by examiner

SYSTEMS AND METHODS FOR NON-INVASIVE CARDIAC ASSESSMENT

CROSS-REFERENCE TO RELATED APPLICATIONS

This application claims the benefit of Provisional U.S. Patent Application No. 62/983,017, filed Feb. 28, 2020, the disclosure of which is incorporated herein by reference in its entirety.

BACKGROUND

Electrophysiology (EP) study may be used to assess the electrical activities of the human heart, from which abnormal conditions such as irregular heartbeats may be detected and treated (e.g., using techniques such as catheter ablation). Common procedures for EP study may involve inserting a catheter into the human body to measure electrical signals directly from the surface of the heart. These procedures are time-consuming, invasive, and prone to causing medical complications. In recent years, electrocardiographic imaging (ECGI) has emerged as a novel technique for measuring cardiac electrical activities. During ECGI, electrodes are placed at different spots of a patient's body (e.g., chest, arms, etc.) to measure electrical potentials of the body surface. Based on the measured body-surface potentials and a heart-torso model that may be derived from computed tomography (CT) images, electrical characteristics of the patient's heart including epicardial electrical potentials, electrograms, and/or isochrones are reconstructed on the heart-torso model, for example, by solving the inverse problem of electrocardiography.

While ECGI has shown great promises as a non-invasive means for imaging cardiac electrophysiology, it only provides epicardial electricity information about a patient's heart and may not reveal endocardial electrical activities of the heart. Moreover, the heart's electrical system is highly sophisticated. Even though tremendous progress has been made in understanding and mapping the heart's electrical system using ECGI techniques, the accuracy of the physics models relied by these techniques is still lacking and the computation burden is often so high that it impedes the deployment of the techniques in many clinical application areas.

Accordingly, it may be highly desirable to develop fast and non-invasive systems and methods for evaluating the electrical activities of the human heart. It may also be desirable to complement the information gained through ECGI with information collected via other cardiac imaging modalities to obtain a holistic view of the human heart and improve the effectiveness and accuracy of cardiac procedures.

SUMMARY

Described herein are neural network-based systems, methods and instrumentalities associated with cardiac assessment. An apparatus as described herein may comprise one or more processors configured to obtain and integrate electrocardiographic imaging (ECGI) information associated with a human heart and magnetic resonance imaging (MRI) information associated with the human heart. The ECGI information may indicate electrical activities of the human heart while the MRI information may indicate biomechanical properties of the human heart. The one or more processors may be configured determine, based on a first machine-learned (ML) model, a correlation between the ECGI information and the MRI information. Based on the determined correlation, the one or more processors may be further configured to generate an integrated representation of the electrical activities and the biomechanical properties of the human heart, where the electrical activities and the biomechanical properties may be geometrically aligned in the integrated representation.

The ECGI information described herein may comprise an electrical map of the human heart and the MRI information described herein may comprise an MRI map indicating strain or tissue properties of the human heart. The one or more processors of the apparatus may be configured to co-register the electrical map with the MRI map, for example, based on respective geometries of the ECGI and MRI maps detected by the artificial neural networks. The integrated representation of the ECGI and MRI information may include a three-dimensional (3D) heart model on the surface of which the electrical map and MRI map may be geometrically aligned. The integrated representation may also include one or more two-dimensional (2D) or three-dimensional (3D) MRI slices and the electrical map and the MRI map may be geometrically aligned in each of the 2D or 3D MRI slices The first ML model described herein may be implemented via one or more artificial neural networks, and may be learned through a training process by matching respective geometrical properties of ECGI training images with MRI training images. The ECGI and MRI training images may comprise a mixture of real medical images and computer-simulated images.

The apparatus described herein may be further configured to predict target ablation locations of the human heart based on a second ML model that is trained to associate the target ablation locations with all or a subset of the electrical activities of the human heart indicated by the ECGI information and all or a subset of the biomechanical properties of the human heart indicated by the MRI information. Responsive to determining the target ablation locations, the apparatus may be configured to indicate the determined ablation locations together with the co-registered ECGI information and MRI information.

BRIEF DESCRIPTION OF THE DRAWINGS

A more detailed understanding of the examples disclosed herein may be obtained from the following description, given by way of example in conjunction with the accompanying drawing.

DETAILED DESCRIPTION

The present disclosure is illustrated by way of example, and not by way of limitation, in the figures of the accompanying drawings. Embodiments may be described herein using one or more specific human anatomical structures such as the human heart as examples, but it should be noted that the techniques disclosed herein are not limited to the example anatomical structures and can be applied to other anatomical structures as well.

Figure 1A:
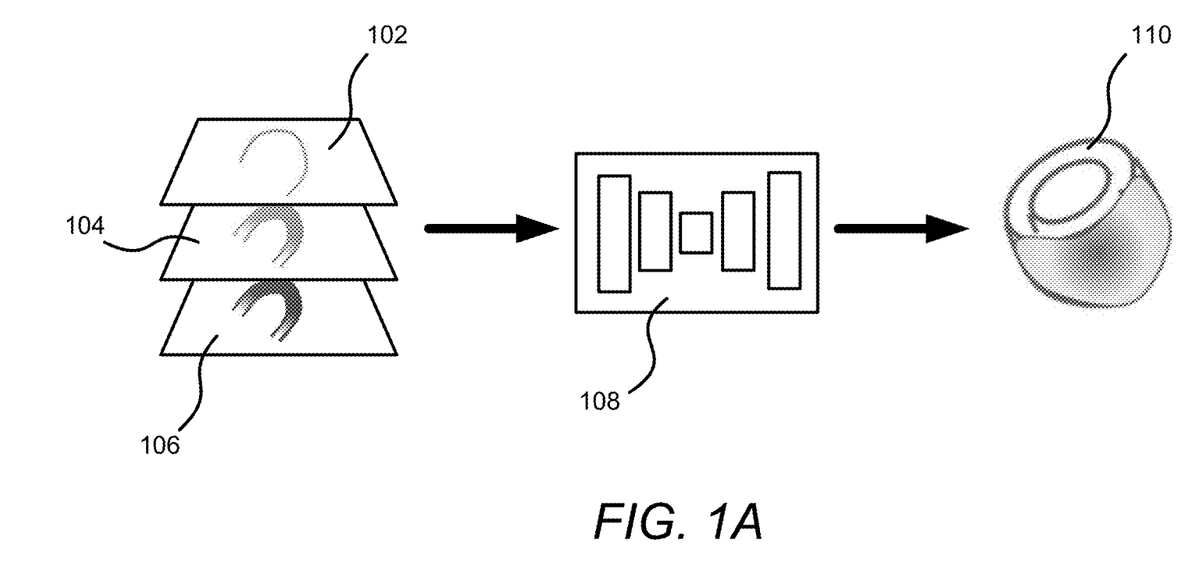
FIG. 1A and FIG. 1B are block diagrams illustrating examples of utilizing artificial intelligence (AI) techniques to integrate electrocardiographic imaging (ECGI) information and magnetic resonance imaging (MRI) information.
Figure 1B:
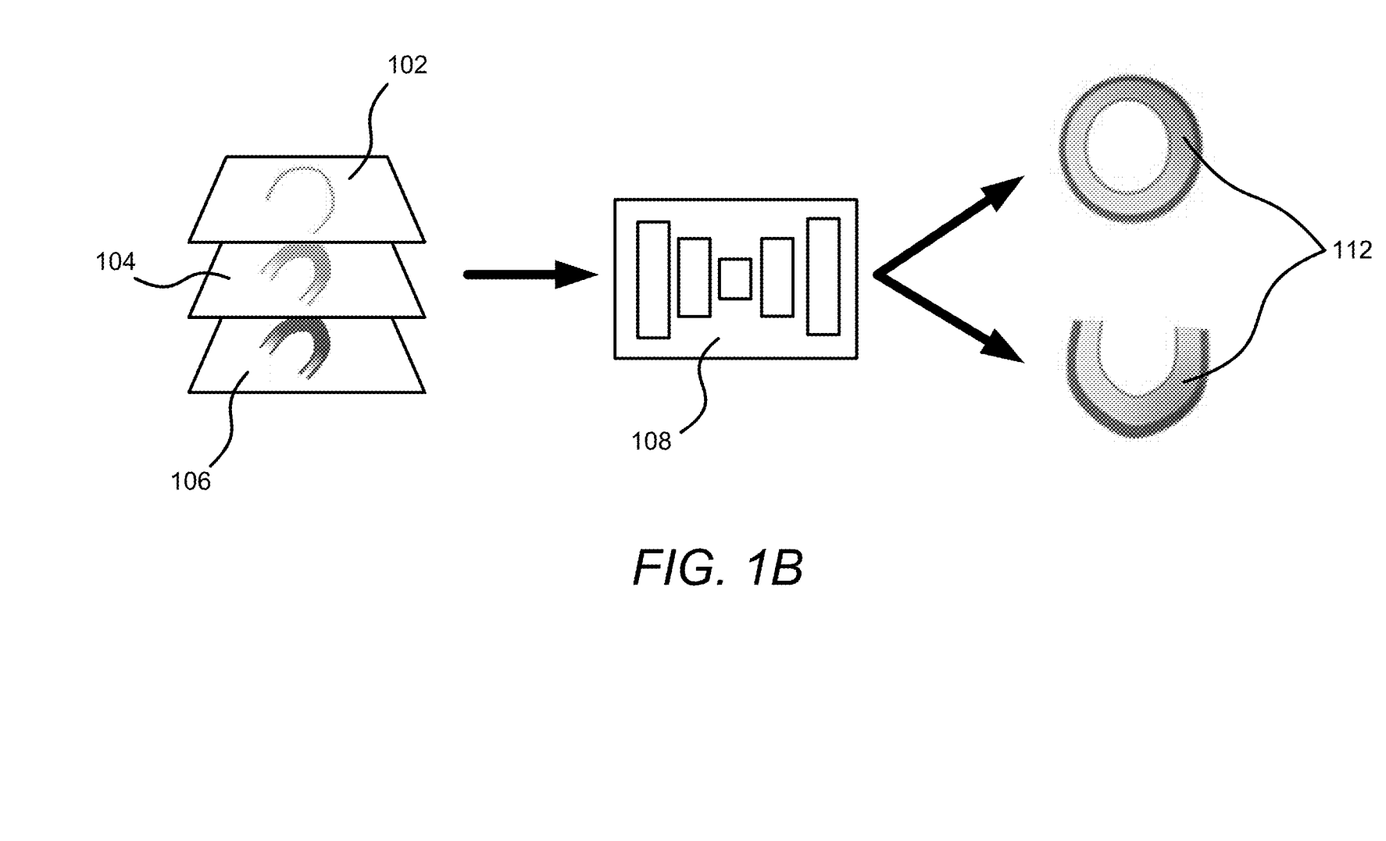

FIGS. 1A and 1B illustrate examples of utilizing artificial intelligence (AI) techniques to integrate electrocardiographic imaging (ECGI) information 102 reconstructed from body-surface potentials with magnetic resonance imaging (MRI) information 104/106 collected via a cardiac MR (cMR) scan. The ECGI information 102 may depict electrical activities of the human heart, which may be used to determine activation and repolarization parameters, abnormal signals, and/or electrogram morphology of the heart. The MRI information 104/106 may indicate biomechanical properties of the heart. For example, the MRI information 104 may indicate the mechanical properties of the heart (e.g., strain, strain rate, etc.) and the MRI information 106 may indicate the tissue characteristics of the heart (e.g., T1, T2, T2*, late-gadolinium-enhancement (LGE), etc.). The ECGI information 102 and MRI information 104/106 may be obtained using various measurement, scan, mapping, and/or reconstruction techniques. For instance, the ECGI information 102 may be obtained by placing electrodes at different areas of a patient's body (e.g., chest, arms, legs, etc.) to measure electrical potentials of the body surface and solving the inverse electrocardiography problem to reconstruct the epicardial electrical activities of the patient's heart on a three-dimensional (3D) model of the patient's heart surface. The 3D heart model may be derived based on the patient's heart-torso geometry (e.g., determinable from computed tomography (CT) images), and the ECGI information thus obtained may include various electrical maps such as an epicardial potential map, an activation map, a repolarization map, etc. that may be indicative of the epicardial electrical potentials, electrograms of the heart, and/or isochrones of the heart. The MRI information 104/106 may be obtained by scanning (e.g., via a magnetic resonance scanner) of the patient's heart at multiple locations (e.g., along a short and/or long axis of the heart) and determining the anatomy and/or tissue properties of the heart based on a sequence of two-dimensional (2D) or three-dimensional (3D) cardiac magnetic resonance (cMR) slices (e.g., cine) produced by the scan. As such, the MRI information may include various MR maps such as a strain map, a T1 map, and/or a T2 map that may provide anatomy as well as function information about the heart (e.g., abnormal strain, T1, and/or T2 values may indicate the existence of scar tissues). When referred herein, a strain map may indicate one or more mechanical properties of the heart, a T1 map may indicate longitudinal tissue relaxation or magnetic spin-lattice relaxation characteristics of the heart, and a T2 map may indicate transverse tissue relaxation or spin-spin relaxation characteristics of the heart.

The ECGI information 102 and the MRI information 104/106 may be provided as input to one or more artificial neural networks 108, which may be configured to implement a machine-learned (ML) model for determining a correlation between the electrical activities of the human heart indicated by the ECGI information and the biomechanical properties (e.g., strain, T1, and/or T2 values) of the human heart indicated by the MRI information. In examples, the ML model (e.g., the one or more artificial neural networks 108) may be configured to take paired ECGI anatomy images or maps (e.g., obtained via CT scans) and MRI images (e.g., regular MRI images and/or MRI maps that may be obtained via MRI scans) as input, and generate transform metrics (e.g., spatial transformation metrics) that may be used to align the ECGI images with the MRI images (e.g., in the anatomy structure domain). In examples, the ML model (e.g., the one or more artificial neural networks 108) may be configured to take paired ECGI anatomy images and MRI images as input and extract respective landmarks (e.g., anatomy landmarks) from the ECGI images and the MRI images. Transform metrics (e.g., spatial transformation metrics) for aligning the ECGI and MRI images may then be determined by aligning the landmarks extracted from the ECGI images with the landmarks extracted from the MRI images. In examples, the ML model (e.g., the one or more artificial neural networks 108) may be configured to take ECGI anatomy images and MRI images as input, and correlate the ECGI and MRI images (e.g., with respect to the anatomy structures depicted in the images) by fitting a heart model (e.g., a 3D heart model) to the ECGI images and the MRI images. Such a heart model may be a 3D deformable heart model constructed from 2D and/or 3D heart images (e.g., using a mesh technique or a pre-trained artificial neural network). The heart model may be parametrized or non-parameterized, and may represent the heart structure of the average population (e.g., as average of multiple patients). For instance, when fitting the heart model to both the ECGI anatomy images and the MRI images, the one or more artificial neural networks 108a may correlate a point on the ECGI images to a point on the MRI images by mapping the point on the ECGI images and the point on the MRI images to respective reference point(s) on the 3D heart model, and determining the correlation (e.g., spatial correlation) between the ECGI point and the MRI point based on the correlation of the corresponding reference point(s) on the 3D heart model.

The artificial neural networks 108 may include one or more convolutional neural networks (CNNs) and each of the CNNs may comprise a plurality of layers. The plurality of layers may include one or more convolutional layers, one or more pooling layers, and/or one or more fully connected layers that are configured to extract respective features from the ECGI information (e.g., one or more ECGI images or maps) and the MRI information (e.g., one or more MRI images or maps such as strain, T1, and/or T2 maps), and determine spatial transformations for co-registering the ECGI features with the MRI features (e.g., to geometrically align the ECGI images/maps with the MRI images/maps). For example, each of the convolutional layers of the artificial neural networks 108 may include a plurality of convolution kernels or filters (e.g., with a kernel size of 3×3 or 5×5) having respective weights. Each of the kernels or filters may be configured to extract a specific feature from an ECGI image/map and/or an MRI image/map, and multiple such kernels and filters may collectively capture increasingly complex features of the ECGI image/map and/or the MRI image/map. The convolution operations may be followed by batch normalization and/or activation (e.g., using a rectified linear unit (ReLU) function), and the features extracted by the convolutional layers (e.g., in the form of one or more feature maps or feature vectors) may be used to determine a spatial relationship (e.g., spatial transformation metrics) between the ECGI image/map and the MRI image/map for linking (e.g., co-registering) all or a subset of the pixels/voxels of the ECGI image/map to those of the MRI image/map.

The ML model, including the weights assigned to each of the kernels or filters of the artificial neural networks 108 layers, may be learned (e.g., offline) from a training dataset that comprises ECGI data (e.g., ECGI images and/or electrical maps) and/or MRI data (e.g., MRI images and/or MRI maps such as strain, T1, and/or T2 maps) collected from real medical cases and/or generated via computer simulation. For example, computer simulation aimed at augmenting the training dataset may start with generating MRI data that are indicative of heart anatomical structures and tissue properties, followed by generating ECGI data that are reflective of electricity activities of the heart in accordance with classic physics models. Various data simulation techniques may be employed to accomplish the data augmentation task. These techniques may include, for example, setting a value to a transformation (e.g., translation, rotation, dense field warping, etc.) and applying the transformation to an existing image to generate a simulated image.

The training of the ML model (e.g., the artificial neural networks 108) may include providing paired ECGI and MRI datasets (e.g., ECGI and MRI images/maps) to the artificial neural networks 108, causing the neural networks to predict a preliminary result (e.g., a spatial relationship or spatial transformation metrics between the ECGI and MRI images/maps), and iteratively adjust (e.g., via backpropagation) the parameters of the neural networks (e.g., weights assigned to various layers of the neural networks) to minimize a predetermined loss function between the preliminary result and an expected result. In examples, the artificial neural networks 108 may be trained an unsupervised manner. For instance, the artificial neural networks 108 may receive an ECGI anatomy training image and an MRI training image (e.g., a regular MRI image or MRI map) and estimate initial metrics for transforming the ECGI anatomy image to align with the MRI image (or vice versa), e.g., in the anatomy structure domain. The artificial neural networks 108 may then determine differences (e.g., with respect to anatomical structures) between the transformed ECGI anatomy image and the input MRI image (or between a transformed MRI image and the input ECGI image), for example, based on mean squared errors between the two images, based on mutual information associated with the two images that indicates the differences in the contents of the images (e.g., even if the images have different contrasts), and/or based on another metric that may be pre-learned to gauge the differences between cross-modality images (e.g., such as the transformed ECGI anatomy image and the input MRI image). The determined differences may then be used to optimize (e.g., via backpropagation) the neural network parameters (e.g., weights), for example, by minimizing the differences.

The artificial neural networks 108 be configured to determine the differences between the transformed ECGI image and the input MRI image (or between a transformed MRI image and the input ECGI image) with respect to the anatomy structures depicted in the two images, even if the two images have different contrasts. In examples, the artificial neural networks 108 may perform a domain transfer on the images (e.g., so that the transformed ECGI image will have the contrast of the input MRI image or the transformed MRI image will have the contrast of the input ECGI image), and determine the mean squared errors between the anatomy structures depicted in the domain-transferred ECGI image and the MRI image (or the domain-transferred MRI image and the ECGI image). In examples, the artificial neural networks 108 may decompose the transformed ECGI image and the input MRI image (or a transformed MRI image and the input ECGI image) to obtain respective contrast information and structure information of the images. The artificial neural networks 108 may then determine the differences between the two images based on their respective structure information (e.g., since the different contrast appearances of the two images may be contained in the contrast information, resulting in the structure information indicating only the anatomy structure differences between the two images).

In examples, the training of the ML model (e.g., the artificial neural networks 108) may include causing the neural networks to extract respective landmarks (e.g., anatomy landmarks) from an input ECGI image and an input MRI image, compare the extracted landmarks with a ground truth (e.g., manually labeled ECGI landmarks and MRI landmarks), and adjust (e.g., via backpropagation) the parameters (e.g., weights) of the artificial neural networks to minimize the difference between the landmarks extracted by the neural networks and the ground truth. The training may also be conducted in an end-to-end and/or unsupervised manner in which landmark extraction and landmark alignment may be combined. For example, the neural networks may extract respective landmarks from an input ECGI image and an input MRI image, predict transform metrics for aligning the landmarks extracted from the ECGI image and the MRI image, and adjusting (e.g., via backpropagation) the parameters (e.g., weights) of the artificial neural networks to minimize the difference between the predicted alignment and a desired alignment (e.g., using one of the input images as the target/desired image, as described herein).

In examples, the training of the ML model (e.g., the artificial neural networks 108) may be conducted utilizing a heart model such as a 3D heart model. The heart model may be a deformable heart model constructed from 2D/3D heart images, and may be parametrized or non-parameterized. During training, the neural networks may fit the heart model to an input ECGI image to determine a correlation between a point on the ECGI image and a point on the 3D heart model. The neural networks may also fit the heart model to an input MRI image to determine a correlation between a point on the MRI image and a point on the 3D heart model. Using the respective points on the 3D heart model that correspond to the ECGI point and the MRI point, the neural networks may determine a correlation (e.g., spatial correlation) between the ECGI point and the MRI point and consequently a correlation between the ECGI image and the MRI image. Similar to the other examples described herein, the training/learning may be driven by minimizing the difference between a predicted correlation and a desired correlation in either supervised or unsupervised manner. Various aspects of the training process for the artificial neural networks 108 and/or the ML model will be described in greater detail below.

Reverting to FIGS. 1A and 1B, the correlation (e.g., spatial transformations) between the ECGI maps 102 and the MRI maps 104/106 predicted by the artificial neural networks 108 may be used to align (e.g., geometrically) respective coordinate systems and/or spatial resolutions of the ECGI maps and MRI maps so that the two sets of data may be integrated to provide a holistic view of the electrical and biomechanical conditions of the heart. This may be possible even if different MR sequences may provide different in-plane and through-plane resolutions, and the MRI maps may have a lower resolution than the ECGI maps. The integrated data may be presented in different formats and/or provided to different receiving devices. FIG. 1A shows an example in which one or more of the MRI maps (e.g., one or more of a strain map, a T1 map, or a T2 map) are projected onto a heart model (e.g., a 3D heart model) reconstructed from the ECGI geometry data to generate an integrated representation 110 in which the electrical activities indicated by the ECGI data and the biomechanical properties indicated by the MRI data may be geometrically aligned (e.g., various spatial resolutions and/or geometries of the ECGI and MRI data may be interpolated and unified). The projection operation may be performed, for example, based on the spatial relationship between the ECGI maps and the MRI maps determined by the artificial neural networks 108 (e.g., via the anatomy co-registration process described herein). For instance, the 3D heart model may represent a system and/or space, and the projection of the ECGI and/or MRI data into the space represented by the 3D heart model may include decomposing the ECGI and/or MRI data to one or more eigen vectors of the space (e.g., the eigen values of the space may represent the ECGI/MRI data).

FIG. 1B shows an example in which aligned ECGI and MRI data are presented in one or more 2D/3D MR slices 112 (e.g., short- and/or long-axis slices) where all or a subset of epicardial, endocardial, and transmural information may be visible. In either of the examples shown in FIG. 1A and FIG. 1B, the aligned information may be presented in a consistent manner. For instance, each map may be presented as a color-coded surface on the 3D heart model or the 2D/3D MR slice(s), the transmural information available on the MRI data or metrics may be projected (e.g., maximumly projected) onto the epicardium and presented on the heart model, and epicardium electricity values may be presented as a thickened color-coded contour of the epicardium. In examples (e.g., when an ECGI map is defined on the epicardium and an MRI map is defined on the epicardium, endocardium, and/or transmural), the MRI image/map may be projected so that the transmural information of the MRI map may be visualized in similar manners as the ECGI map. The projection may be performed, for example, by determining a maximum along the radial direction of the heart and using the maximum to represent the pixel at the intersection of the radial line and the epicardium.

The integrated (e.g., co-registered) ECGI and MRI information may be used to facilitate various clinical applications including, for example, non-invasive EP and intervention planning (e.g., ablation planning). And since intervention procedures may be planned based on ECGI and native MRI scans (e.g., cine, T1, T2, etc.) that require no image contrast, patients with special medical conditions (e.g., compromised kidney functions) may no longer need to take Gadolinium (Gd) based image contrast agent (e.g., required for late gadolinium enhanced (LGE) CMR scans) during intervention operations.

Figure 2:
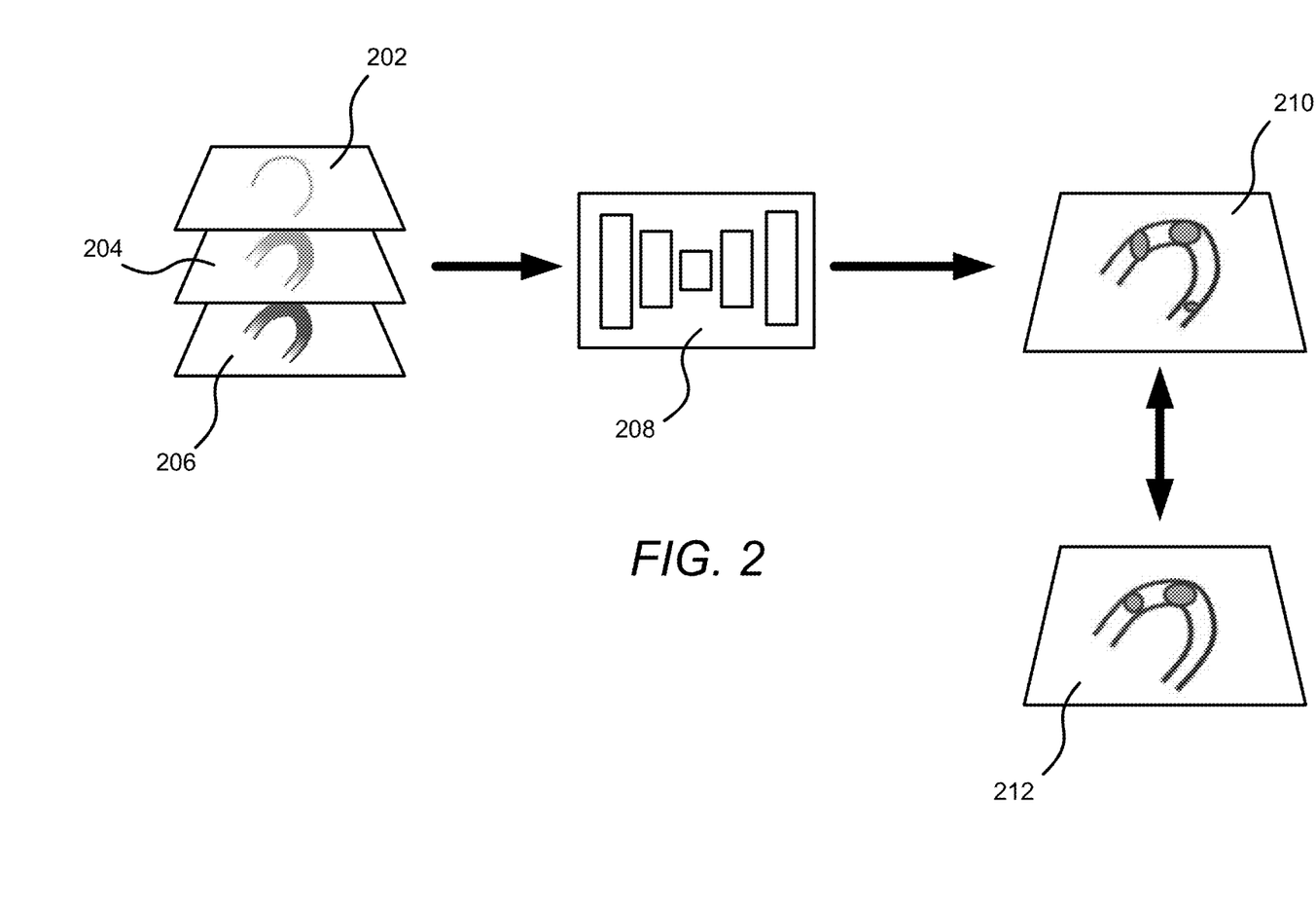
FIG. 2 is a block diagram illustrating an example of utilizing AI techniques to predict radio frequency (RF) ablation targets in a human heart based on co-registered ECGI information and MRI information.

FIG. 2 shows an example of utilizing AI techniques to predict radio frequency (RF) ablation targets in a heart based on co-registered ECGI information 102 and MRI information (e.g., mechanical properties 104 and/or tissue properties 106) about the heart. The ECGI information 102 and the MRI information 104/106 may be obtained and/or co-registered using the techniques described herein, and provided (e.g., as input) to one or more artificial neural networks 208. The artificial neural networks 208 may be configured to implement an ML model for determining a correlation between certain electrical activities (e.g., indicated by the ECGI) and biomechanical properties (e.g., indicated by the MRI) and candidate ablation locations, and providing an indication 210 of the candidate ablation locations. The indication 210 may be overlaid with (e.g., superimposed upon) co-registered ECGI and MRI information (e.g., on the integrated representation 110 in FIG. 1A and/or 112 in FIG. 1B) to provide reference and guidance for the ablation operation.

The artificial neural networks 208 may include one or more convolutional neural networks (CNNs) each comprising a plurality of layers. The plurality of layers may include one or more convolutional layers, one or more pooling layers, one or more fully connected layers, and/or one or more regression layers that are configured to predict a candidate ablation location based on patterns detected in the co-registered ECGI and MRI information. For example, each of the convolutional layers of the artificial neural networks 208 may include a plurality of convolution kernels or filters (e.g., with a kernel size of 3×3 or 5×5) having respective assigned weights. Each of the kernels or filters may be configured to extract a specific feature from an ECGI map and/or an MRI map, and multiple such kernels and filters may collectively capture increasingly complex features of the ECGI map and/or the MRI map. The convolution operations may be followed by batch normalization and/or activation (e.g., using a rectified linear unit (ReLU) function), and the features extracted by the convolutional layers (e.g., in the form of one or more feature maps or feature vectors) may be provided to a regression layer to estimate an ablation location corresponding to detected electrical and/or mechanical features and/or patterns. In examples, the regression layer may be associated with a non-linear activation function such as a sigmoid function for converting a scalar value determined by the artificial neural networks 208 (e.g., by other layers of the artificial neural networks) into a probability (e.g., with a value between 0 and 1) indicating the likelihood of a location being an ablation target. As such, the output of the artificial neural networks 208 may be a probability map, with one or more pixels (e.g., each pixel) of the map representing the likelihood of corresponding locations of the heart being an ablation site.

The ablation prediction model described herein, including the weights assigned to each of the kernel or filters of the artificial neural networks 208, may be learned (e.g., offline) from a training dataset that comprises co-registered ECGI data (e.g., ECGI electrical maps) and MRI data (e.g., strain, T1, and/or T2 maps) as well as actual ablation sites 212 that may serve as ground truth for the training. The training data may be collected from real medical cases/operations, and/or generated via computer simulation. For example, ablation site maps recorded during EP operations may be obtained (e.g., on 3D EP anatomy images). The ablation site maps (e.g., the EP anatomy images) may be co-registered with ECGI maps and/or MRI maps using the techniques described herein (e.g., if the EP images are not already aligned with the ECGI images), before being used to train the artificial neural networks 208.

The training of the prediction model and/or the neural networks 208 may include providing co-registered ECGI and MRI datasets (e.g., ECGI and MRI maps) to the artificial neural networks 208 (e.g., the input maps may be concatenated along a channel direction before being provided to the neural networks), predicting preliminary ablation locations based on the input data and initial network parameters (e.g., weights assigned to various layers of the neural networks), and iteratively adjusting (e.g., via backpropagation) the parameters of the neural networks to minimize a predetermined loss function between the predicted ablation locations and ground truth 212 (e.g., actual ablation sites) associated with the prediction. The loss function may be based on, for example, mean squared errors (MSE), cross-entropy, root mean square errors, L1/L2 norm, etc., and the optimization of the network parameters may be performed through a backpropagation process in accordance with a gradient descent (e.g., a stochastic gradient descent) of the loss function. Various aspects of the training process for the artificial neural networks 208 and/or the ML model will be described in greater detail below.

AI-based techniques may also be applied to mimic the electrical system of the heart (e.g., predict or estimate EP measurements) and/or to create a virtual heart based on the ECGI and/or MRI information described herein. Such an AI-predicted electrical system may eliminate the needs for complex physics models and/or multi-scale (e.g., cell, structure, organ, etc.) finite element analysis in order to conduct cardiac assessment. And since EP measurements may be estimated based on non-invasively collected ECGI and MRI information, the number of invasive procedures such as catheter-based data collection and/or mapping procedures may be reduced or completely avoided. Additionally, a virtual heart constructed using the AI techniques may be used to simulate changes or results that may be induced by an intervention procedure (e.g., such as induced ventricle tachycardial (VT) and/or ablation procedures), thus decreasing the risks of medical complications or morbidity.

Figure 3:
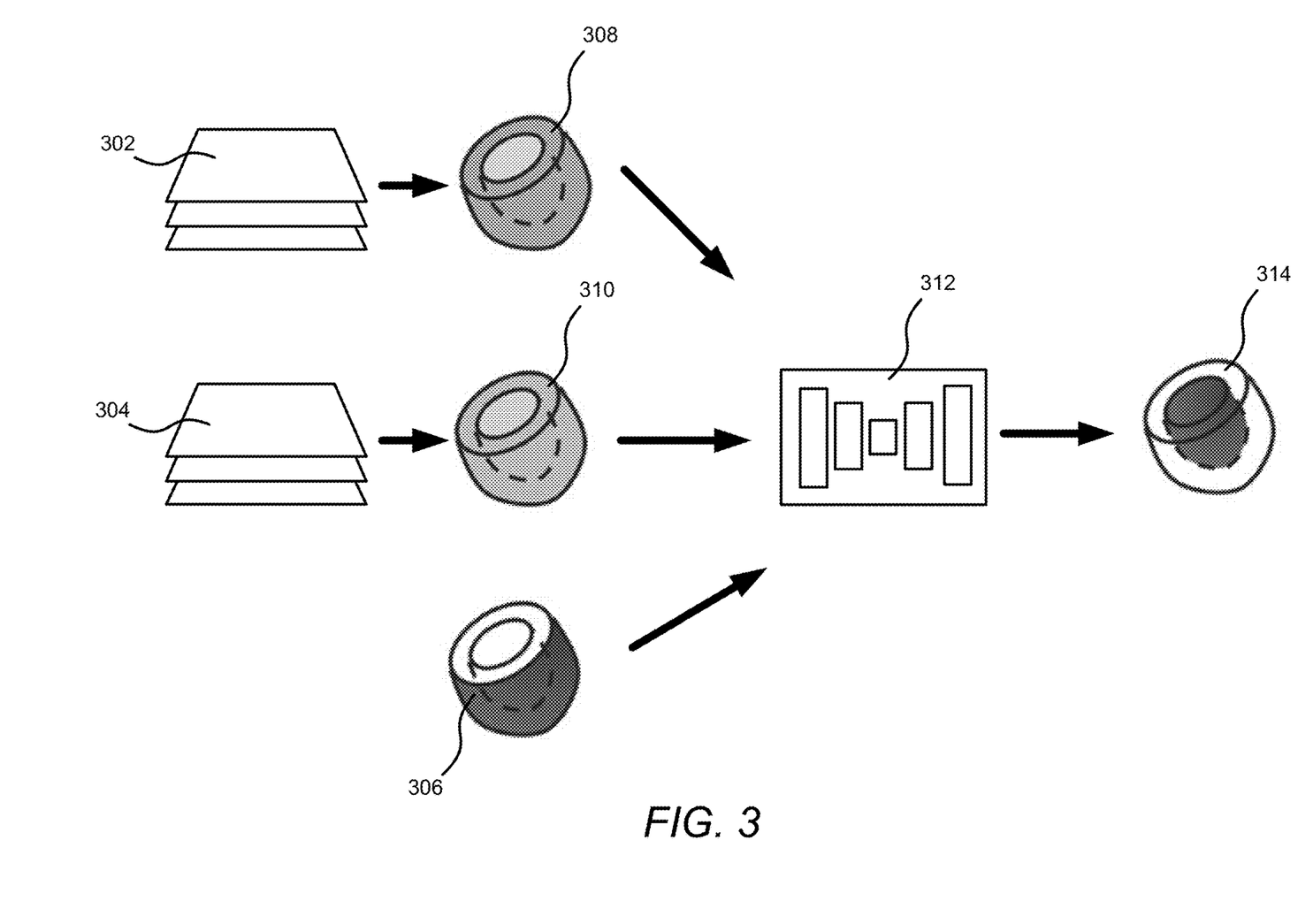
FIG. 3 is a block diagram illustrating an example of utilizing AI techniques to predict EP measurements of a heart and/or to simulate a virtual heart.

FIG. 3 shows an example of utilizing AI techniques to predict EP measurements (e.g., endocardial electrical activities) of a heart and/or a virtual heart based on non-invasively collected MRI information (e.g., 2D MR slices 302 and 304) and ECGI information 306. In examples, the MR slices 302 may provide 3D heart anatomy information 308, the MR slices 304 may provide 3D tissue property information 310 (e.g., T1 and T2 values) about the heart, and the ECGI information 306 may depict electrical activities (e.g., epicardial electrical activities) of the heart. Various interpolation techniques may be applied to obtain the 3D heart anatomy information 308 based on the MR slices 302. The interpolation may allow for determination of pixel/voxel values not captured by the MR slices based on neighboring slices/pixels. The interpolation techniques may include linear/cubic interpolation techniques and/or super-resolution based techniques. The MR anatomy information 308, MR tissue property information 310, and ECGI information 306 may be provided as input to one or more neural networks 312 pre-trained to take the role of classis physics models and output (e.g., directly) predicted EP measurements 314 that would have been collected invasively under a conventional, computer simulation based approach. Additionally, or alternatively, the artificial neural networks 312 may be trained act as a patient-specific virtual heart, which may take planned ablation locations as input (e.g., as part of the input information) and output predicted electrical activities (e.g., in the form of an electrical map) that may be induced by an ablation operation.

Due to the complexity of the heart electrical system, a large amount of MRI data, ECGI data, and/or invasively measured electricity data may be used to train the artificial neural networks 312. Computer simulation may be used to augment the training data collected from real medical cases/patients. Such simulation may start with generating heart anatomy and tissue property information, followed by simulating the electricity activities of the heart based on classic physics models. For example, electrical activities of the heart may be simulated using techniques such as finite element analysis at multiple scales (e.g., at cell, structure, and/or organ levels).

Figure 4:
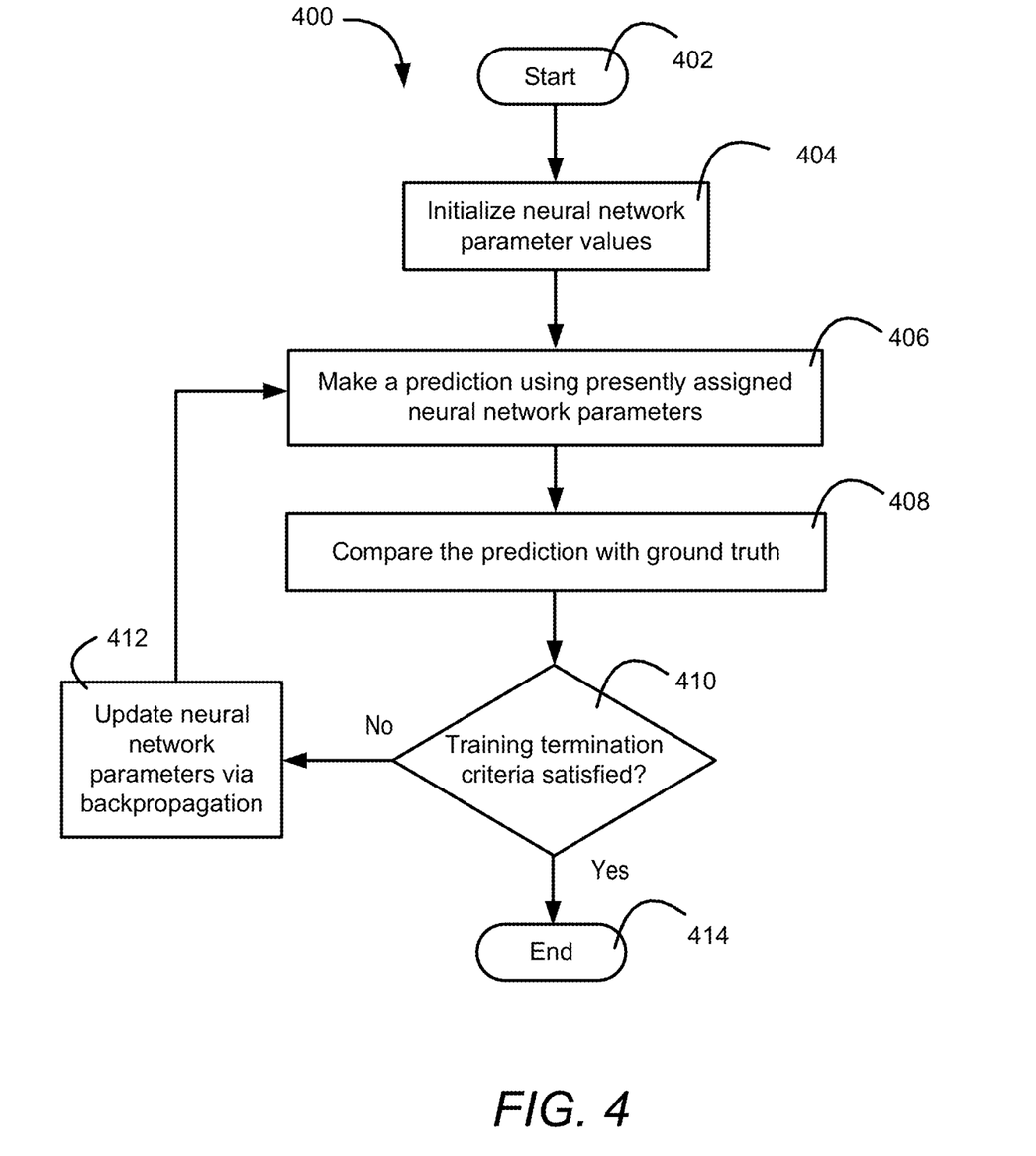
FIG. 4 is a flow diagram illustrating an example process for training a neural network that may be configured to perform the functions described herein.

The artificial neural networks described herein (e.g., the neural networks 108 of FIGS. 1A and 1B, the neural networks 208 of FIG. 2, and/or the neural networks 312 of FIG. 3) may be trained to optimize their parameters (e.g., weights associated with the filters/layers of the neural networks) for performing the various identification, prediction, or estimation tasks described herein. FIG. 4 illustrates an example process 400 for training a neural network described. The process 400 may start at 402 and, at 404, the neural network may initialize its operating parameters such as the weights associated with one or more filters or kernels of the neural network. The parameters may be initialized, for example, based on samples from one or more probability distributions or parameter values of another neural network with a similar architecture. At 406, the neural network may receive a set of training data (e.g., ECGI and MRI maps) at the input, process the input training data through the various layers of the neural network, and make a prediction for a target result (e.g., a spatial transformation, an ablation location, etc.) using presently assigned parameters. At 408, the neural network may determine adjustments to be made to the presently assigned parameters based on a loss function and a gradient descent (e.g., a stochastic gradient decent) associated with the loss function. For example, the loss function may be implemented based on a mean squared error (MSE), a Dice ratio, a cross entropy, etc. between the prediction and a ground truth associated with the prediction. At 410, the neural network may carry out the adjustments to the presently assigned parameters, for example, via a backpropagation process. At 412, the neural network may determine whether one or more training termination criteria are satisfied. For example, the neural network may determine that the training termination criteria are satisfied if the neural network has completed a pre-determined number of training iterations, if the difference between the predicted values and the ground truth values is below a predetermined threshold, or if the change in the value of the loss function between two training iterations falls below a predetermined threshold. If the determination at 412 is that the training termination criteria are not satisfied, the neural network may return to 406. If the determination at 412 is that the training termination criteria are satisfied, the neural network may end the training process 400 at 414.

Figure 5:
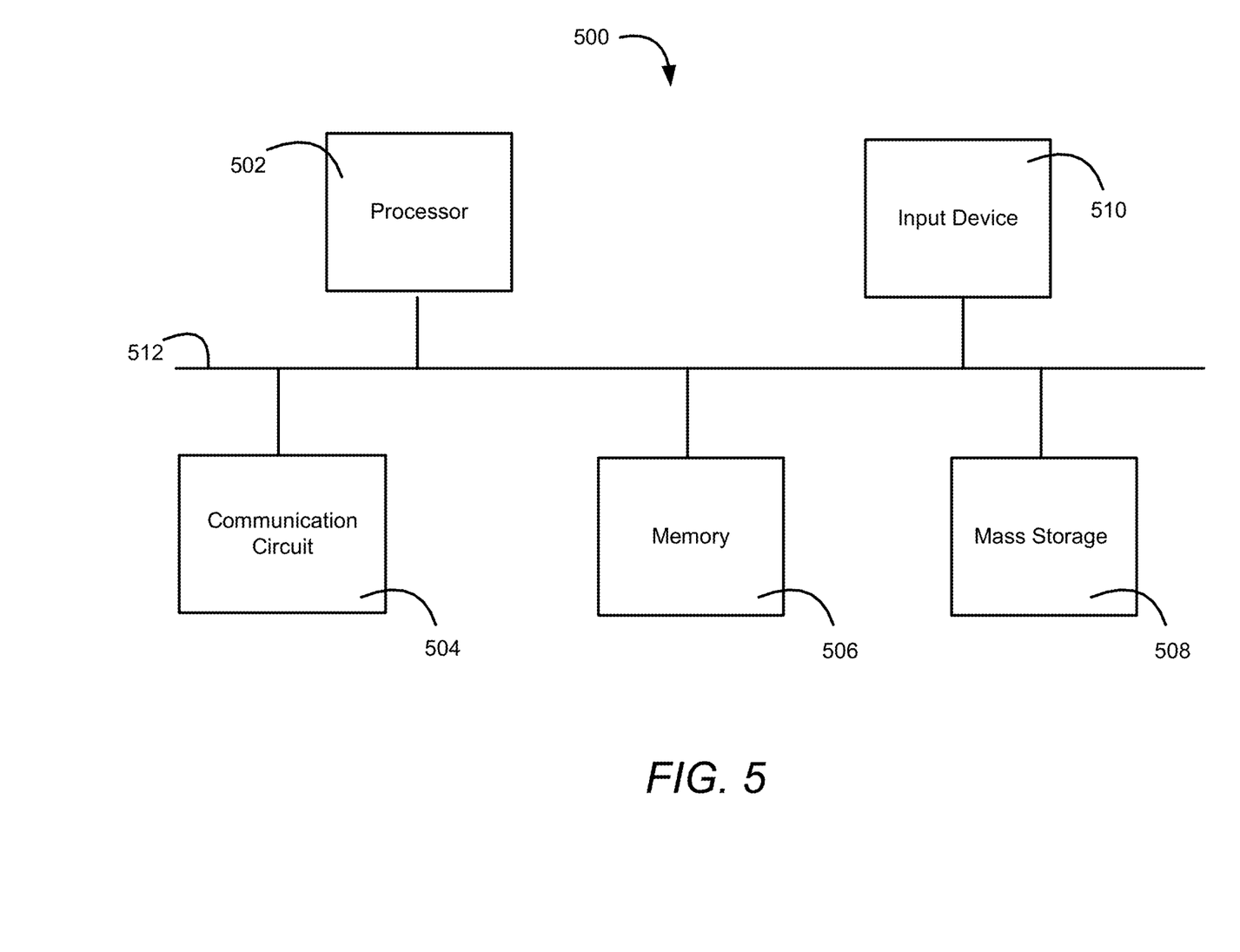
FIG. 5 is a block diagram illustrating example components of a system/apparatus that may be configured to perform the functions described herein.

A system or apparatus configured to perform the functions described herein may be implemented using one or more processors, one or more storage devices, and/or other suitable accessory devices such as display devices, communication devices, input/output devices, etc. FIG. 5 is a block diagram illustrating such a system or apparatus 500. As shown, the system/apparatus 500 may include a processor (e.g., one or more processors) 502, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The system/apparatus 500 may further include a communication circuit 504, a memory 506, a mass storage device 508, an input device 510, and/or a communication link 512 (e.g., a communication bus) over which the one or more components shown in FIG. 5 may exchange information. The communication circuit 504 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 506 may include a storage medium configured to store machine-readable instructions that, when executed, cause the processor 502 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 508 may include one or more magnetic disks such as one or more internal hard disks, one or more removable disks, one or more magneto-optical disks, one or more CD-ROM or DVD-ROM disks, etc., on which instructions and/or data may be stored to facilitate the operation of the processor 502. The input device 510 may include a keyboard, a mouse, a voice-controlled input device, a touch sensitive input device (e.g., a touch screen), and/or the like for receiving user inputs to the system/apparatus 500.

It should be noted that the system/apparatus 500 may operate as a standalone device or may be connected (e.g., networked or clustered) with other computation devices to perform the functions described herein. And even though only one instance of each component is shown in FIG. 5, a skilled person in the art will understand that the system/apparatus 500 may include multiple instances of one or more of the components shown in the figure. Furthermore, although the examples are described herein with reference to various types of neural networks, various types of layers, and/or various tasks being performed by certain types of neural networks or layers, those references are made merely for illustration purposes and not meant to limit the scope of the disclosure. In addition, the operation of the example system/apparatus 500 is depicted and described herein with a specific order. It should be appreciated, however, that these operations may occur in various orders, concurrently, and/or with other operations not presented or described herein. And not all operations that the system/apparatus 500 is capable of performing are depicted and described herein, and not all illustrated operations are required to be performed by the system.

For simplicity of explanation, the operation of the example system is depicted and described herein with a specific order. It should be appreciated, however, that these operations may occur in various orders, concurrently, and/or with other operations not presented or described herein. Furthermore, it should be noted that not all operations that the system is capable of performing are depicted and described herein, and not all illustrated operations are required to be performed by the system.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus configured to facilitate cardiac assessment, comprising one or more processors, wherein the one or more processors are configured to:
   obtain an electrocardiographic imaging (ECGI) map associated with a human heart, wherein the ECGI map indicates electrical activities of the human heart;
   obtain a magnetic resonance imaging (MRI) map associated with the human heart, wherein the MRI map indicates biomechanical properties of the human heart;
   determine, based on a first machine-learned (ML) model, a correlation between the ECGI map and the MRI map, wherein the determination comprises identifying, based on the first ML model, a first plurality of points in the ECGI map and a second plurality of points in the MRI map, and correlating the first plurality of points with the second plurality of points; and
   generate an integrated representation of the electrical activities and the biomechanical properties of the human heart in accordance with the determined correlation between the ECGI map and the MRI map, wherein the electrical activities and the biomechanical properties are geometrically aligned in the integrated representation.

2. The apparatus of claim 1, wherein the MRI map includes a strain map, a T1 map, or a T2 map associated with the human heart.

3. The apparatus of claim 1, wherein the one or more processors being configured to determine the correlation between the ECGI map and the MRI map comprises the one or more processors being configured to spatially transform at least one of ECGI map or the MRI map so as to align the first plurality of points in the ECGI map with the second plurality of points in the MRI map in the integrated representation.

4. The apparatus of claim 1, wherein the integrated representation includes a three-dimensional (3D) heart model, wherein the correlation between the ECGI map and the MRI map is determined based on the 3D heart model, and wherein the ECGI map and the MRI map are geometrically aligned on the 3D heart model.

5. The apparatus of claim 1, wherein the integrated representation includes multiple two-dimensional (2D) MRI slice images, and wherein the ECGI map and the MRI map are geometrically aligned in each of the 2D MRI slice images.

6. The apparatus of claim 3, wherein the one or more processors being configured to spatially transform at least one of the ECGI map or the MRI map comprises the one or more processors being configured to align respective coordinate systems or resolutions of the ECGI map and the MRI map.

7. The apparatus of claim 6, wherein the first ML model is learned using a plurality of paired ECGI training images and MRI training images, and wherein learning the first ML model comprises determining transformation metrics for aligning each of the ECGI training images with a corresponding one of the MRI training images.

8. The apparatus of claim 1, wherein the electrical activities indicated by the ECGI map are associated with an epicardium of the human heart, the biomechanical properties indicated by the MRI map include transmural biomechanical properties of the human heart, and wherein the one or more processors being configured to generate the integrated representation of the electrical activities and the biomechanical properties of the human heart comprises the one or more processors being configured to manipulate the transmural biomechanical properties such that both the electrical activities and the transmural biomechanical properties of the human heart are visualized with respect to the epicardium in the integrated representation.

9. The apparatus of claim 1, wherein the one or more processors are further configured to predict a target ablation location of the human heart based on a second ML model, the second ML model trained to associate the target ablation location with all or a subset of the electrical activities of the human heart indicated by the ECGI map and all or a subset of the biomechanical properties of the human heart indicated by the MRI map.

10. The apparatus of claim 9, wherein the one or more processors are further configured to indicate the target ablation location in the integrated representation.

11. A method for facilitating cardiac assessment, comprising:
obtaining an electrocardiographic imaging (ECGI) map associated with a human heart, wherein the ECGI map indicates electrical activities of the human heart;
obtaining a magnetic resonance imaging (MRI) map associated with the human heart, wherein the MRI map indicates biomechanical properties of the human heart;
determining, based on a first machine-learned (ML) model, a correlation between the ECGI map and the MRI map, wherein the determination comprises identifying, based on the first ML model, a first plurality of points in the ECGI map and a second plurality of points in the MRI map, and correlating the first plurality of points with the second plurality of points; and
generating an integrated representation of the electrical activities and the biomechanical properties of the human heart in accordance with the determined correlation between the ECGI map and the MRI map, wherein the electrical activities and the biomechanical properties are geometrically aligned in the integrated representation.

12. The method of claim 11, wherein the MRI map includes a strain map, a T1 map, or a T2 map associated with the human heart.

13. The method of claim 11, wherein determining the correlation between the ECGI map and the MRI map comprises spatially transforming at least one of the ECGI map or the MRI map so as to align the first plurality of points in the ECGI map with the second plurality of points in the MRI map in the integrated representation.

14. The method of claim 11, wherein the integrated representation includes a three-dimensional (3D) heart model, wherein the correlation between the ECGI map and the MRI map is determined based on the 3D heart model, and wherein the ECGI map and the MRI map are geometrically aligned on the 3D heart model.

15. The method of claim 11, wherein the integrated representation includes multiple two-dimensional (2D) MRI slice images, and wherein the ECGI map and the MRI map are geometrically aligned in each of the 2D MRI slice images.

16. The method of claim 13, wherein spatially transforming at least one of the ECGI map or the MRI map comprises aligning respective coordinate systems or resolutions of the ECGI map and the MRI map.

17. The method of claim 16, wherein the first ML model is learned using a plurality of paired ECGI training images and MRI training images, and wherein learning the first ML model comprises determining transformation metrics for aligning each of the ECGI training images with a corresponding one of the MRI training images.

18. The method of claim 11, wherein the electrical activities indicated by the ECGI map are associated with an epicardium of the human heart, wherein the biomechanical properties indicated by the MRI map include transmural biomechanical properties of the human heart, and wherein generating the integrated representation of the electrical activities and the biomechanical properties of the human heart comprises manipulating the transmural biomechanical properties such that both the electrical activities and the transmural biomechanical properties of the human heart are visualized with respect to the epicardium in the integrated representation.

19. The method of claim 11, further comprising predicting a target ablation location of the human heart based on a second ML model, wherein the second ML model is trained to associate the target ablation location with all or a subset of the electrical activities of the human heart indicated by the ECGI map and all or a subset of the biomechanical properties of the human heart indicated by the MRI map.

20. The method of claim 19, further comprising indicating the target ablation location in the integrated representation.

* * * * *